US008762167B2

(12) United States Patent
Blander et al.

(10) Patent No.: US 8,762,167 B2
(45) Date of Patent: Jun. 24, 2014

(54) METHODS AND SYSTEMS FOR GENERATION OF PERSONALIZED HEALTH PLANS

(75) Inventors: Gil Blander, Lexington, MA (US); Christian Reich, Cambridge, MA (US); David Lester, Kew (AU)

(73) Assignee: Segterra Inc., Lexington, MA (US)

( * ) Notice: Subject to any disclaimer, the term of this patent is extended or adjusted under 35 U.S.C. 154(b) by 0 days.

(21) Appl. No.: 13/190,996

(22) Filed: Jul. 26, 2011

(65) Prior Publication Data

US 2012/0130732 A1  May 24, 2012

Related U.S. Application Data

(60) Provisional application No. 61/368,002, filed on Jul. 27, 2010.

(51) Int. Cl.
G06Q 50/22 (2012.01)
G06Q 10/10 (2012.01)
G06F 19/10 (2011.01)
G06F 19/00 (2011.01)

(52) U.S. Cl.
CPC ............ *G06Q 50/22* (2013.01); *G06F 19/3475* (2013.01); *G06F 19/3481* (2013.01); *G06Q 10/10* (2013.01); *G06F 19/10* (2013.01)
USPC .................... 705/2; 705/3; 435/6.11; 702/20; 703/6; 715/771

(58) Field of Classification Search
CPC .............................. G06F 19/363; G06Q 50/22
USPC .................... 705/3; 435/6.11; 702/20; 703/6; 715/771
See application file for complete search history.

(56) References Cited

U.S. PATENT DOCUMENTS

| 5,706,822 | A | 1/1998 | Khavari |
| 5,890,997 | A | 4/1999 | Roth |
| 6,746,371 | B1 | 6/2004 | Brown et al. |
| 7,054,758 | B2 * | 5/2006 | Gill-Garrison et al. ......... 702/20 |

(Continued)

FOREIGN PATENT DOCUMENTS

| JP | 2002-222265 | 8/2002 |
| JP | 2004-240862 | 8/2004 |

(Continued)

OTHER PUBLICATIONS

Google patents search result, Mar. 18, 2013.*

(Continued)

*Primary Examiner* — Dilek B Cobanoglu
(74) *Attorney, Agent, or Firm* — Fish & Richardson P.C.

(57) ABSTRACT

Personalized, health and performance programs are generated for individuals based on various biomarkers and performance and lifestyle assessments. In one embodiment, a diagnostic test of blood or other biological specimen(s) is used to determine key biological marker levels. Information and assessments of the user's physical performance, life style and health and wellness goals is also collected and provided to an expert system that matches the biomarker levels and assessments to a knowledgebase of scientific knowledge about biomarker levels and health and fitness outcomes. Personal recommendations and advice on nutrition and exercise is then generated, which may be used to help individuals reach their diet, fitness, and wellness goals and improve their physical and mental performance and well being in measurable ways.

25 Claims, 12 Drawing Sheets

(56) References Cited

U.S. PATENT DOCUMENTS

| | | |
|---|---|---|
| 7,201,579 B1 | 4/2007 | Boyum |
| 7,247,023 B2 | 7/2007 | Peplinski et al. |
| 7,412,511 B2 | 8/2008 | Curry |
| 7,413,438 B2 | 8/2008 | Bisogno |
| 7,591,760 B2 | 9/2009 | Gordon et al. |
| 8,129,191 B2 * | 3/2012 | Sheard et al. ............ 436/86 |
| 8,234,129 B2 * | 7/2012 | Michon et al. ............ 705/3 |
| 2003/0187683 A1 | 10/2003 | Kirchhoff et al. |
| 2003/0204412 A1 | 10/2003 | Brier |
| 2004/0010420 A1 | 1/2004 | Rooks |
| 2005/0095628 A1 * | 5/2005 | Krempin et al. ........... 435/6 |
| 2006/0122468 A1 | 6/2006 | Tavor |
| 2006/0287883 A1 | 12/2006 | Turgiss et al. |
| 2007/0179351 A1 | 8/2007 | Kil et al. |
| 2007/0191689 A1 | 8/2007 | Elitok |
| 2008/0091463 A1 | 4/2008 | Shakamuri |
| 2008/0162186 A1 | 7/2008 | Jones |
| 2008/0195594 A1 | 8/2008 | Gerjets et al. |
| 2009/0076335 A1 | 3/2009 | Schwarzberg et al. |
| 2009/0131089 A1 | 5/2009 | Micali et al. |
| 2009/0132284 A1 | 5/2009 | Fey et al. |
| 2009/0198516 A1 | 8/2009 | Greenholtz |
| 2009/0216559 A1 * | 8/2009 | Krempin et al. ........... 705/3 |
| 2009/0276487 A1 | 11/2009 | Jensen et al. |
| 2010/0255475 A1 * | 10/2010 | Kornman et al. ........... 435/6 |
| 2011/0093249 A1 * | 4/2011 | Holmes et al. ............. 703/6 |
| 2011/0145747 A1 * | 6/2011 | Wong et al. ............ 715/771 |
| 2012/0286953 A1 * | 11/2012 | Bousamra et al. ........ 340/540 |

FOREIGN PATENT DOCUMENTS

| | | |
|---|---|---|
| JP | 2006-119773 | 5/2006 |
| JP | 2006-345973 | 12/2006 |
| JP | 2009-244964 | 10/2009 |
| WO | WO01/16855 | 3/2001 |
| WO | WO02/091276 | 11/2002 |

OTHER PUBLICATIONS

Proquest search, May 2, 2014.*

Probst, Y., et al., "Overview of Computerized Dietary Assessment Programs for Research and Practice in Nutrition Education," Journal of Nutrition Education and Behavior, 37(1), 20-26, 2005.

* cited by examiner

Example of Athletic Clinical Trial Datasets Analysis

| Record ID | Subjects | Biomarkers | Supplements | Outcomes |
|---|---|---|---|---|
| 3341317 | Iron (ferritin) deficient non-anemic runners, ferritin < 20 ng/ml | Ferritin | Iron (ferrous sulfate), 975 mg/day, 4 weeks | Endurance time improvement in supplement treated runners; decline in non-treated runners |

If Ferritin < 20 ng/ml → recommend iron (ferrous sulfate) at 975 mg/day for 4 weeks

FIG. 7 segplan EAT BETTER EXERCISE BETTER FEEL BETTER

Welcome Gil Blander | Log Out

| MY PROGRESS | MY GOALS | MY FOOD | MY EXERCISE | MY SETTINGS |

MY PROGRESS

YOUR VALUES AGAINST YOUR OPTIMUM

| BLOOD FACTOR | | LAST TEST | 3 MONTHS AGO | 6 MONTHS AGO | OPTIMUM | GOAL |
|---|---|---|---|---|---|---|
| CK | +200 | 900 | 980 | 1050 | 660-700 | Decrease by 200 |
| Vitamin B12 | -45 | 605 | 520 | 545 | 650-780 | Increase by 45 |
| Serum Ferritin | -4 | 51 | 49 | 40 | 55-70 | Increase by 4 |
| ● Needs improvement  ○ Almost there | | | | | | |

[Run Test Again]   [View All Values]

TODAY'S MENU

BREAKFAST
Bran Flakes Cereal  Quantity: ½ cup
Whole Wheat Toast  Quantity: 1 slice
Banana  Quantity: ½ unit
More Menu Items

[View Full Menu]

TODAY'S EXERCISE

| FITNESS GOAL | EXERCISE | INTENSITY | DURATION |
|---|---|---|---|
| Endurance | Endurance sport | Heart rate of 123 per min | 30 Mins |
| Strength | 8 Muscle groups | 70% of 1RM | 2 Sets with 10 reps |
| Flexibility | 5 Muscle groups | Comfortable | 10 Reps, 10-30 secs each rep |

View a list of your endurance exercise, strength exercise and flexibility exercise options.

[View Detailed Program]

↺ Repeat the Segplan process regularly to improve performance and reach your potential.

©Segterra, Inc. All rights reserved. Segplan is a personal nutrition model by Segterra.

Privacy | Terms | Who are we? | Support | Contact Us

FIG. 9

Overview of your blood work
*Click on a blood factor for a detailed description.*

Your latest test was run on: Apr 05, 2011

My Progress

| Blood factor | Your values compared to your optimum | Unit | Latest test | Optimum | Required Action |
|---|---|---|---|---|---|
| Glucose | | mg/dL | 92 | 81.3-94.2 | Maintain |
| Calcium | -0.01 | mg/dL | 9.2 | 9.21-9.8 | Increase by 0.01 |
| Magnesium | +0.25 | mg/dL | 2.1 | 1.59-1.85 | Decrease by 0.25 |
| Creatine kinase | | U/L | 66 | 50-250 | Maintain |
| Vitamin B12 | | pg/mL | 336 | 325-626 | Maintain |
| Folic acid | +5.79 | ng/mL | 19.6 | 7.02-13.81 | Decrease by 5.79 |
| Vitamin D | -13 | ng/mL | 19 | 32-42 | Increase by 13 |
| Ferritin | | ng/mL | 118 | 28-124 | Maintain |
| Total Cholesterol | +21 | mg/dL | 214 | 155-193 | Decrease by 21 |
| Hemoglobin | +0.3 | g/dL | 16.6 | 14.6-16.3 | Decrease by 0.3 |

● Needs improvement  ○ Almost there  ⊘ Optimal range

FIG. 10 segplan EAT BETTER  EXERCISE BETTER  FEEL BETTER        Welcome Gil Blander | Log Out

| MY PROGRESS | MY GOALS | MY FOOD | MY EXERCISE | MY SETTINGS |

Recommended Food
Your recommended intake of nutrients and supplements.                 Your recommendations were updated on: Jun 10, 2010     🛒 5 items

| FOOD | SHOPPING LIST | | | | MENU | | | |
|---|---|---|---|---|---|---|---|---|
| FOOD TO EAT | | UNIT | KCAL | IRON | VITAMIN D | PREFERENCE | SHOPPING LIST |
| ▼ Fish | | | | | | | |
| Salmon Sockeye, raw | | 3 oz | 169 | 4.00 mg | 13.0 µg | Dislike | Add |
| Mackerel Atlantic, raw | | .5 fillet | 168 | 0.47 mg | 18.2 µg | Dislike | Add |
| Swordfish, raw | | 1 fillet | 205 | 1.63 mg | 16.1 µg | Dislike | Add |
| Tuna Bluefin, raw | | 1 piece | 121 | 0.81 mg | 9.7 µg | Dislike | Add |
| Sardine, canned, drained | | 3 oz | 144 | 1.02 mg | 5.7 µg | Dislike | Add |
| ► Chocolate Malt Drink Mix | | 1 cup | 208 | 2.92 mg | 4.8 µg | Dislike | Add |
| ▼ Formulated Fitness Bar | | 1 cup | 389 | 17.3 mg | 23.8 µg | Dislike | Add |
| Mars Snickers Marathon Honey Nut Oat Bar | | 1 bar | 388 | 9.58 mg | 2.9 µg | Dislike | Add |
| Mars Snickers Marathon Energy Bar, all flavors | | 1 bar | 389 | 16.31 mg | 4.5 µg | Dislike | Add |
| Luna Bar, nuts over chocolate bar | | 1 bar | 386 | 14.2 mg | 3.1 µg | Dislike | Add |
| Mars Snickers Marathon, protein performance bar, caramel nut rush | | 1 bar | 403 | 10.13 mg | 3.8 µg | Dislike | Add |
| Slim-Fast Optima Meal Bar, milk chocolate peanut | | 1 bar | 415 | 4.98 mg | 5.4 µg | Dislike | Add |
| High Fiber, Chewy, Oats and Chocolate Bar | | 1 bar | 386 | 17.95 mg | 2.1 µg | Dislike | Add |
| Mars Cocoavia, chocolate almond snack | | 1 bar | 343 | 1.88 mg | 1.0 µg | Dislike | Add |
| ► Mushroom | | 1 bar | 396 | 1.63 mg | 0.3 µg | Dislike | Add |
| | | 1 piece | 31 | 12.18 mg | 5.3 µg | Dislike | Add |

| SUPPLEMENT TO TAKE | SUPPLIER | AMOUNT | TAKE | TAKE WITH | # PER DAY | SHOPPING LIST |
|---|---|---|---|---|---|---|
| Creatine | Wonder (C546) | 1000 mg | After Meal | Gatorade | 3 | Add |
| Vitamin B12 | Wonder (A125) | 1000 mg | During Meal | Water | 1 (Morning) | Add |
| Iron | Feosol (B23C) | 975 mg | Before Meal | Orange Juice | 1 (Evening) | Add |

Exclude food with [Select from list ▼]

Export  Print                                                                    << 1-10  11-20  21-30  31-40 >>

Find out how your Segplan values        Changes to your life? Find out how        Subscribe to our daily or weekly        Looking for recipes?
have improved for only $99              your recommendations will change.         Segplan reminders:                      View trusted free recipes online,
                                                                                  Via Email                               complete with ratings, reviews
[Run Test Again]  ⬆                     [Update My Settings]  ⬆                   Via SMS                                 and cooking tips.

METHODS AND SYSTEMS FOR GENERATION OF PERSONALIZED HEALTH PLANS

CROSS-REFERENCE TO RELATED APPLICATIONS

This application claims priority to and the benefit of U.S. provisional patent application with Ser. No. 61/368,002 filed on Jul. 27, 2010, entitled "Methods and Systems for Generation of Personalized Health Plans."

FIELD OF INVENTION

The present invention relates generally to computer systems and processes for collecting information from a proprietary diagnostic panel and questionnaire that may be used for the purposes of enhancing of personal wellness through the creation of science based individualized lifestyle, fitness, dietary and nutrient plans.

BACKGROUND OF THE INVENTION

Current annual health care costs in the US are more than $3 trillion dollars and expected to increase over the next ten years to over $4 trillion. As of today, more than half of all Americans suffer from one or more chronic diseases and more than 75% of health care spending is to treat chronic conditions including cardiovascular disease and stroke, cancer, obesity, arthritis and diabetes. These serious diseases are often treatable but not always curable. Thus, an even greater burden befalls Americans from the disability and diminished quality of life resulting from chronic disease. These increased healthcare costs do not include costs due to loss of productivity resulting from chronic disease. The World Health Organization has estimated that eliminating certain major risk factors for chronic disease would result in an 80% reduction in the instances of heart disease, stroke, and type-2 diabetes, and a more than 40% reduction in cancer cases. These risk factors are linked to modifiable health behaviors that, if changed, can dramatically reduce the risk and prevalence of chronic disease.

A Center for Disease Control report identified four modifiable health risk behaviors that are responsible for much of the illness, suffering, and early death related to chronic diseases: 1) lack of physical activity, 2) poor nutrition, 3) tobacco use, and 4) excessive alcohol consumption. For example, frequent physical activity has been shown to increase longevity, help control weight, reduce risks for cardiovascular disease, type 2 diabetes, metabolic syndrome, and some cancers, strengthen bones and muscles, improve mental health and mood, improve one's ability to perform daily activities, and to prevent falls among older adults. Balanced nutrition can help lower the risk for many chronic diseases, including heart disease, stroke, some cancers, diabetes, and osteoporosis. For example, it has been established that the increased consumption of fruits and vegetables helps reduce the risk for heart disease and certain cancers.

The U.S. Department of Health and Human Services recognized that preventive medicine and evidence-based medicine will become an important part of the healthcare system, and established the U.S. Preventive Services Task Force agency to oversee, define and implement a variety of preventive medicine measures.

The role of exercise and physical activity in the prevention and treatment of cardiovascular disease is well established and its significance as a preventive measure is widely recognized. In addition, the correlation between athletic performance, body composition, and nutrition status has also been firmly established. The effect of balanced nutrition and its effect on the health of the population has also been subject of many studies. Further, population studies have identified certain blood/plasma biomarkers that are related to balanced nutrition and metabolism, as well as the presence of vitamins and micronutrients such as vitamin D, Iron, selenium, copper and zinc. The present invention leverages existing population-based evidence and provides a new, personalized approach to nutrition and exercise to improve health and wellness and prevent chronic diseases.

SUMMARY OF THE INVENTION

The present invention provides a computer-implemented and web-based personalized nutrition and exercise program and comprehensive wellness assessment. A unique panel of biomarkers from the user's blood or other biological specimen (such as: urine, buccal and nasal samples, exhalants, stool, tissues, organs, hair, nail clippings, or any other cells or fluids—whether collected for research purposes or as residual specimens from diagnostic, therapeutic, or surgical procedures) or devices capturing biological/biomedical activities, is assessed and provides information regarding the presence of vitamins, minerals, nutrients, cytokines and other messenger molecules. By biomarker we are inferring a biomarker, or biological marker, which is in general a substance used as an indicator of a biological state. It is a characteristic that is objectively measured and evaluated as an indicator of normal or impaired biological processes responses to an intervention of food, lifestyle or exercise. This biomarker information is paired and collected along with personal information about nutrition habits, wellness, physical fitness, and exercise regimens. Subsequently, an expert IT systems analyses process, derived from systems biology and artificial intelligence, is used to evaluate the collected data The expert analytic system includes a knowledgebase and an inference engine that provides optimal food, supplement, life style, and exercise recommendations for an individual according to their personal biology, physiology and personal habits.

The biomarker levels are collected through a blood test or test of other biological specimen(s) as defined above. Responses to a questionnaire provide information about the demographic, nutritional and physical habits of the individual. The web-based application provides the individual with her personalized optimal nutrition, supplement, life style, and physical training regime by matching her profile with the knowledgebase of facts about known relationships among biological specimen, demographic, and phenotypic data manually derived from scientific publications, databases and clinical trials.

Therefore, in one aspect of the present invention, a system facilitates the derivation of a personalized health and fitness plan for an individual. The system includes a data storage device for storing an electronic knowledgebase of medical and health data from various sources as well as for storing a set of questions. The system also includes an inference engine for a subset of the set of questions to send to the individual based on the knowledgebase and biomarker data gathered for the individual. The inference engine further generates lifestyle recommendations for the individual based on the biomarker data and the answers to the subset of questions. The system further enables transmission of these recommendations to the individual.

In some implementations, the system contains biomarker data for the same biomarkers and individual from different points in time. In further implementations, the computerized comparison includes comparison of these two different sets of biomarker data.

In certain embodiments, the biomarker data is gathered from blood or some other biological specimen of the individual. In certain embodiments, the system includes creatine kinase or ferritin as biomarkers. In other embodiments, the questions presented to the individual include questions about demographic data or questions about athletic activity. In still other embodiments, the lifestyle recommendations include dietary recommendations or exercise recommendations.

In another aspect of the present invention, a computer-implemented method facilitates the derivation of a personalized health and fitness plan for an individual. The method includes collecting biomarker data for the individual and determining questions to present to the individual based on a comparison between that biomarker data and an electronic knowledgebase of medical and health data from various sources. The method also includes presenting the questions to the individual and receiving the answers. The method further includes generating lifestyle recommendations for the individual based on the biomarker data and answers to questions. The method finally includes transmitting the recommendations to the user.

The method may, in some cases, include collecting a second set of biomarker data from the individual for the same biomarkers and comparing these two sets of biomarker data to discern the difference. In certain embodiments, the biomarker data is gathered from blood or some other biological specimen of the individual. In certain embodiments, the system includes creatine kinase or ferritin as biomarkers. In other embodiments, the questions presented to the individual include questions about demographic data or questions about athletic activity. In still other embodiments, the lifestyle recommendations include dietary recommendations, supplements recommendations or exercise recommendations. In some embodiments the biomarkers include biometric measurements. Examples of biomarkers are selected from, but not limited to: Blood pressure, heart rate, exhaled volume, body temperature, perspiration rate, skin conductivity. In some embodiments of the invention biomarker characteristics and profiles collected may be indicative of a disease process and could be used to detect such processes. Examples of diseases are selected but not limited to metabolic diseases, cancer, anemia, cardiovascular diseases, diabetes. In some embodiments biomarkers will comprise SNP biomarkers (DNA based). The most useful biomarkers in this group are SNPs that are associated with metabolism and energy.

It is to be understood that both the foregoing general description of the invention and the following detailed descriptions are exemplary, but are not restrictive, of the invention.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the inventions.

FIG. 7 illustrates an exemplary athletic clinical trial dataset component.

FIG. 9 illustrates an exemplary website home page in accordance with one embodiment of the invention.

FIG. 10 illustrates an exemplary "My progress" web page in accordance with one embodiment of the invention.

FIG. 11 illustrates an exemplary "My food" web page in accordance with one embodiment of the invention.

Figure 12:
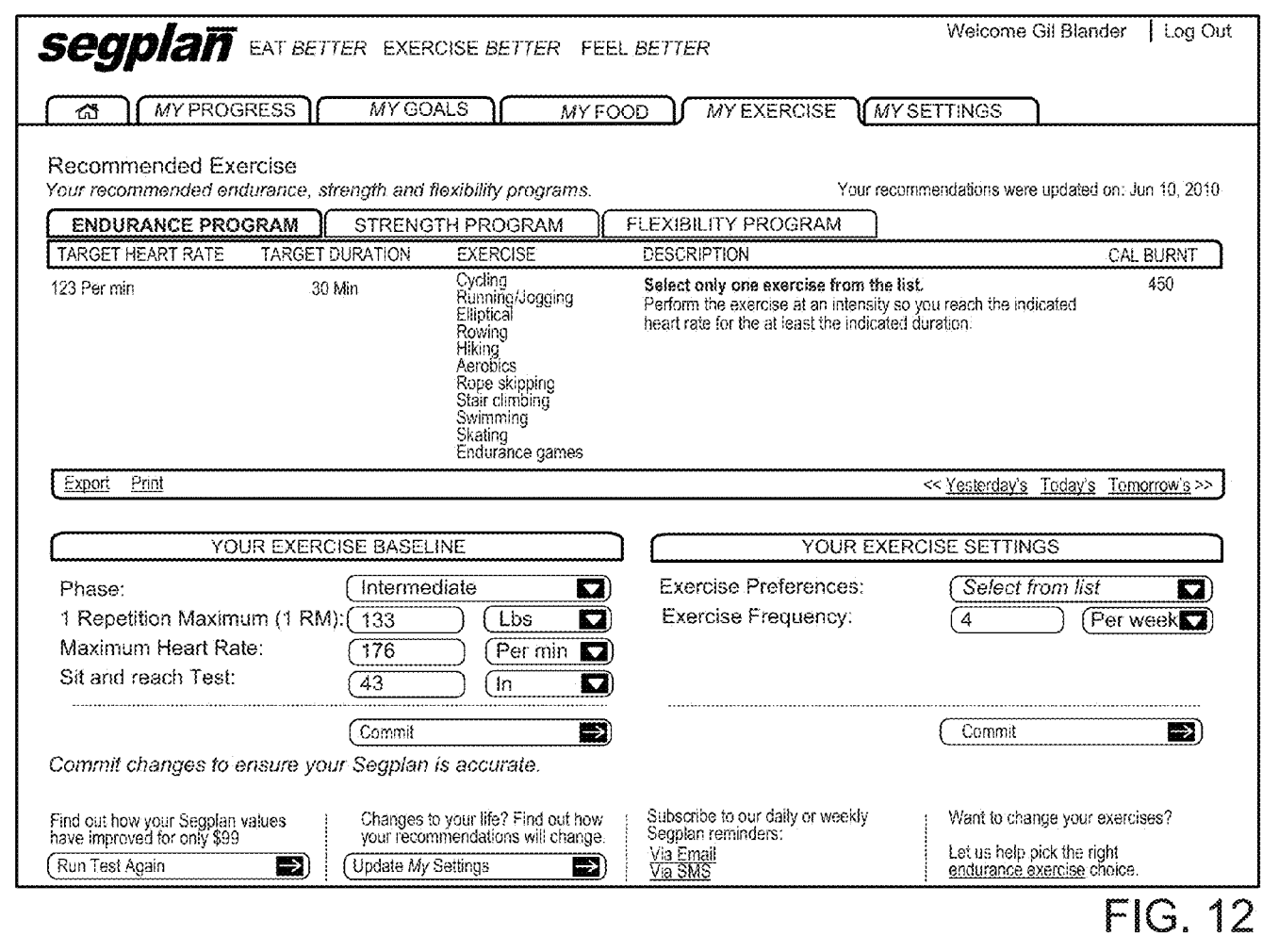

FIG. 12 illustrates an exemplary "My exercise" web page in accordance with one embodiment of the invention.

Appendix A illustrates example of biomarkers.

DETAILED DESCRIPTION OF THE INVENTION

The detailed description set forth below, in connection with the associated drawings, is intended to provide a description of the presently-preferred embodiments of the invention, and is in no way intended to limit the forms in which the present invention may be construed or used. Accordingly, it is well-understood by those with ordinary skill in the art that the same or equivalent functions may be accomplished by different embodiments that are also intended to be encompassed within the spirit and scope of the present invention. Moreover, with respect to particular method steps, it is readily understood by those with skill in the art that the steps may be performed in any order, and are not limited to any particular order unless expressly stated or otherwise inherent within the steps. Reference will now be made in detail to the preferred embodiments of the present invention, examples of which are illustrated in the accompanying drawings.

Figure 1:
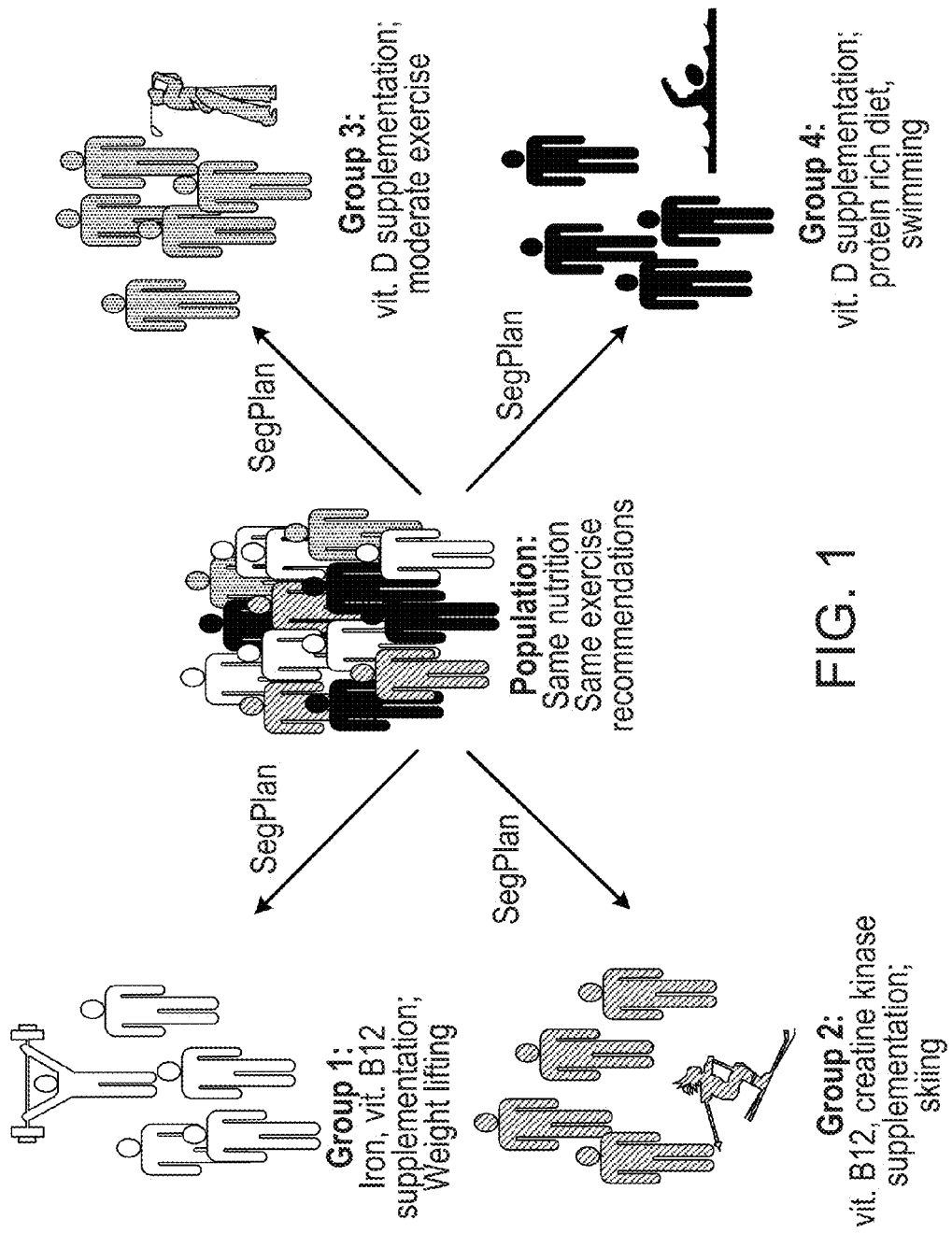
FIG. 1 illustrates the invention's individualized nutrition and exercise approach.

FIG. 1 illustrates the use of a personalized biofeedback approach to improve a user's health and implement a preventive regimen. Conventional approaches to recommending nutrition, exercise, and supplements are population-based statistics and do not take into account an individual's characteristics, such as the metabolism and fitness status. Embodiments of the invention go well beyond this traditional approach and generate a personalized nutrition and physical training program based on biomarkers in the blood or other biological specimens, demographic information, as well as the nutritional and physical fitness habits of the individual.

Figure 2:
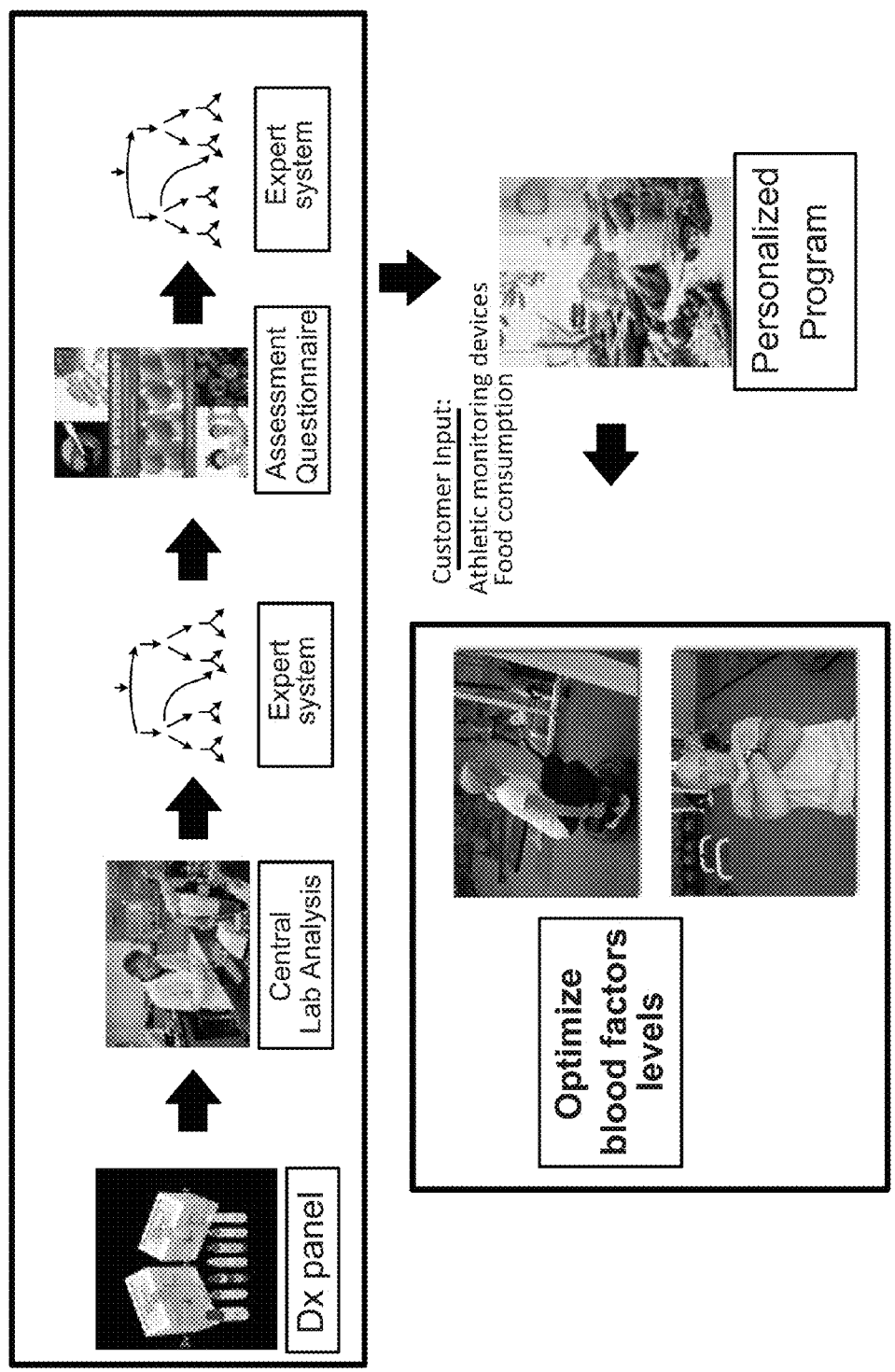
FIG. 2 illustrates an exemplary schematic diagram of the invention workflow.

FIG. 2 illustrates a process flow for implementing one embodiment of the present invention. In this embodiment, blood or other biological specimens of a user are tested for the diagnostic panel (table 1 or 2). Subsequently, the test results are run through an expert system that generates a tailored questionnaire to add information about the specific biology of the user. The tailored questionnaire can then be presented to the user in order to receive answers to the questionnaire. The answers to the questionnaire and the test results are run through the expert system again to generate a set of recommendations to optimize the blood or specimen results and to improve fitness and wellness. This improves over the existing approaches by generating these recommendations based on the additional knowledge provided by the specimen results and questionnaire answers. Existing approaches may use only basic information such as age, height, and weight and thus not provide the user specific recommendations possible with this invention.

Figure 3:
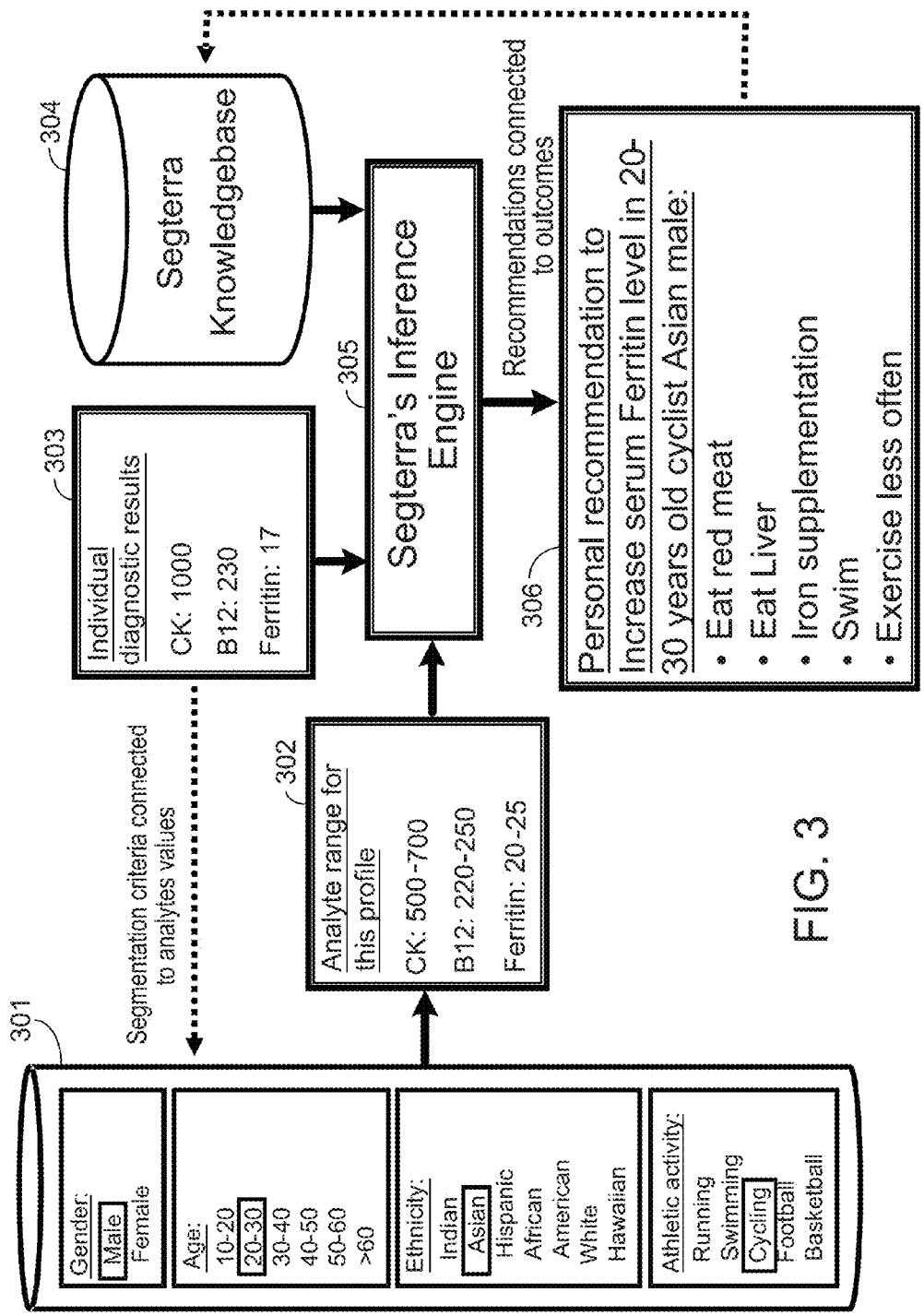
FIG. 3 illustrates is an exemplary approach to the invention's personalized algorithm workflow.

FIG. 3 illustrates an expert system in accordance with one embodiment of the invention that matches biomarkers with personal information of the user. The data store 301 contains data for various categories of information about users, such as gender, age, ethnicity, and type of athletic activity. The expert system in FIG. 3 further has the ability to store relationships between various instances of the information in the data store 301 and store an analyte range 302 for those related instances of information. A set of related instances of information may be termed a "profile" for the purposes of the expert system. As illustrated in FIG. 3, the expert system further has the ability to process individual diagnostic results 303. These individual diagnostic results may result from a blood or other specimen diagnostic panel. As illustrated in FIG. 3, the expert system further has access to a knowledgebase 304 which may contain information regarding previous user recommendations and monitored results. As illustrated in FIG. 3, the expert system has an inference engine 305 that receives analyte range 302, individual diagnostic results 303, and information from knowledgebase 304 in order to produce personal recommendations 306.

In one embodiment of the invention, the expert system as illustrated in FIG. 3 uses answers provided by the user to a questionnaire in order to determine which profile from data store 301 is most applicable to the user. In such an embodiment, the expert system may then retrieve an analyte range 302 specific to this applicable profile. Accordingly, inference engine 305 may then compare the analyte range 302 with the individual diagnostic results 303 and information from knowledgebase 304 in order to determine analyte deficiencies of the specific user and personal recommendations 306 that may consist of activities to correct those deficiencies. In another embodiment of the invention, inference engine 305 may compare analyte range 302, individual diagnostic results 303, and information from knowledgebase 304, in order to produce personal recommendations 306 without specific analyte deficiencies targeted by personal recommendations 306.

In one embodiment of the invention, knowledgebase 304 may contain information regarding relationships between biomarkers, food, supplements, and outcomes. Such outcomes may include changes in athletic performance, well-being, sleep, and mental stability. The information in knowledgebase 304 may be collected from scientific research publications, guidelines issued by medical associations, and large healthcare-derived databases of biomarkers, nutrition, fitness and wellness data. In one embodiment of the invention, inference engine 305 may use artificial intelligence algorithms in order to determine, based on analyst range 302, individual diagnostic results 303, and knowledgebase 304, what interventions can optimize the fitness and wellness of the user. These artificial intelligence algorithms may use any number of machine learning and systems biology inference methods well known in the art in order to generate effective inferences based on analyte range 302, individual diagnostic results 303, and knowledgebase 304. As illustrated in FIG. 3, the expert system may also store the personal recommendations 306 in knowledgebase 304 in order to provide comparison of personal recommendations 306 and individual diagnostic results 303 that may be received by the expert system at a later time for the same user. This follow-up monitoring has the advantage of enabling positive feedback for each individual to increase compliance with a healthy lifestyle.

In one embodiment of the invention, knowledgebase 304 may be constructed using a relational database system containing data organized in tables relating to individual concepts, their relationships to each other, additional qualifiers to these relationships, and references to the peer-reviewed article, clinical study or database from which they were curated. These concepts may include such topics as food, supplements, biomarkers, and outcomes, their relationships to each other. These relationships between concepts may include such items as contains, increases, optimizes at certain level, and releases. In such an embodiment of the invention, knowledgebase 304 may be constructed using several techniques, including: (i) manually entering findings into the system from scientific papers and clinical trials about concepts and their interaction (simplified example: concept1='low serum iron' relationship='causes' concept2=decrease in endurance performance'), (ii) by converting information from other databases (e.g. content of food), and (iii) automatically from accumulation of customer data including previous data processed by the expert system (e.g. information about success rates of certain recommendations). If a relational database management system is used for the construction of knowledgebase 304 or data store 301, any off-the-shelf product such as MySQL Database, Microsoft SQL Server, or IBM DB2 database may be used. It is foreseen that a relational database management system may be chosen for particular technical benefits provided as to size of storage on disk or performance of data retrieval. Non-relational database management system solutions are also foreseen that make use of alternative storage and data access techniques.

In one embodiment of the invention, the validity of the facts collected and the markers used may be strengthened by confirming data in knowledgebase 304 using gene expression microarray experiments. These markers may be either directly implicated, or they are inferred as in the same pathway as the markers captured in the knowledgebase (example 2).

When the input data changes, either through addition of new biomarker measurements or new personal information (wellness and fitness assessments and goals), inference engine 305 may use both forward and backward chaining to derive new or updated recommendations. For example, to infer the right food to battle a certain marker imbalance, inference engine 305 may use backward chaining. In order to detect whether this marker may be influenced through different kinds of exercises or whether it is affected by ethnic background, inference engine 305 may use forward chaining.

When making these inferences, the expert system may use a mechanism that can make complete deductions (any logically valid implication) instead of sound deductions (only deriving correct results). To decide between the various available deductions, inference engine 305 may apply a weighting system based on the success or failure of past personal recommendations 306, thereby creating a self-learning system. In order determine the success or failure of personal recommendations 306, it is foreseen that the system may store the relationship between individual diagnostic results 303 and personal recommendations 306 as well as an identifier for the user so that subsequent individual diagnostic results 303 for the same user can be compared to the previous individual diagnostic results 303 and previous personal recommendations 306 in order to determine the changes in the user's biomarkers after having received personal recommendations 306. Such knowledge may allow the system to modify the personal recommendations 306 given to individual users in subsequent processing of their individual diagnostic results 303 in order to improve the health outcomes of those users.

Figure 4:
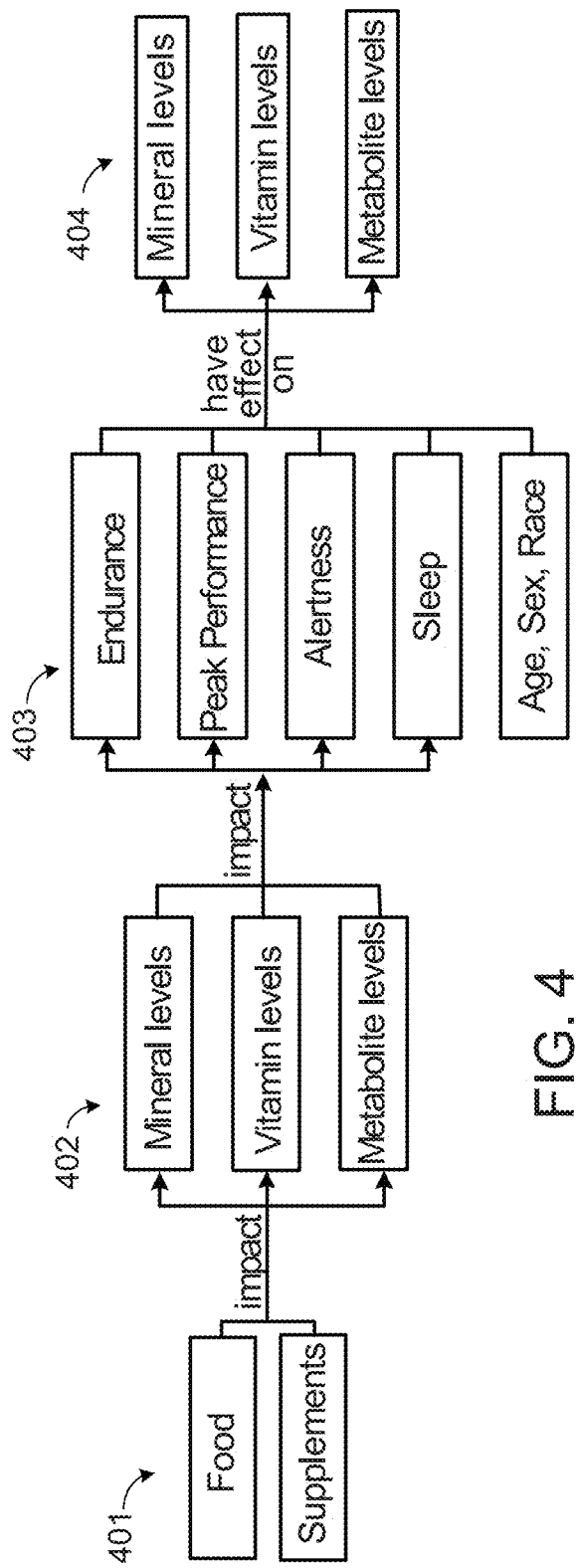
FIG. 4 illustrates knowledgebase of facts in accordance with one embodiment of the invention.

FIG. 4 illustrates exemplary facts in a simplified example of knowledgebase 304. In this particular embodiment, knowledgebase 304 contains data about food and supplements 401, biomarkers 402, outcomes 403, and further biomarkers 404. As illustrated in FIG. 4, knowledgebase 304 of this example represents relationships between these various entities, namely, how food and supplements 401 influence biomarkers 402, how biomarkers 402 have an effect on outcomes 403, and how these activities as well as demographic information have an influence on biomarkers 404.

Figure 5:
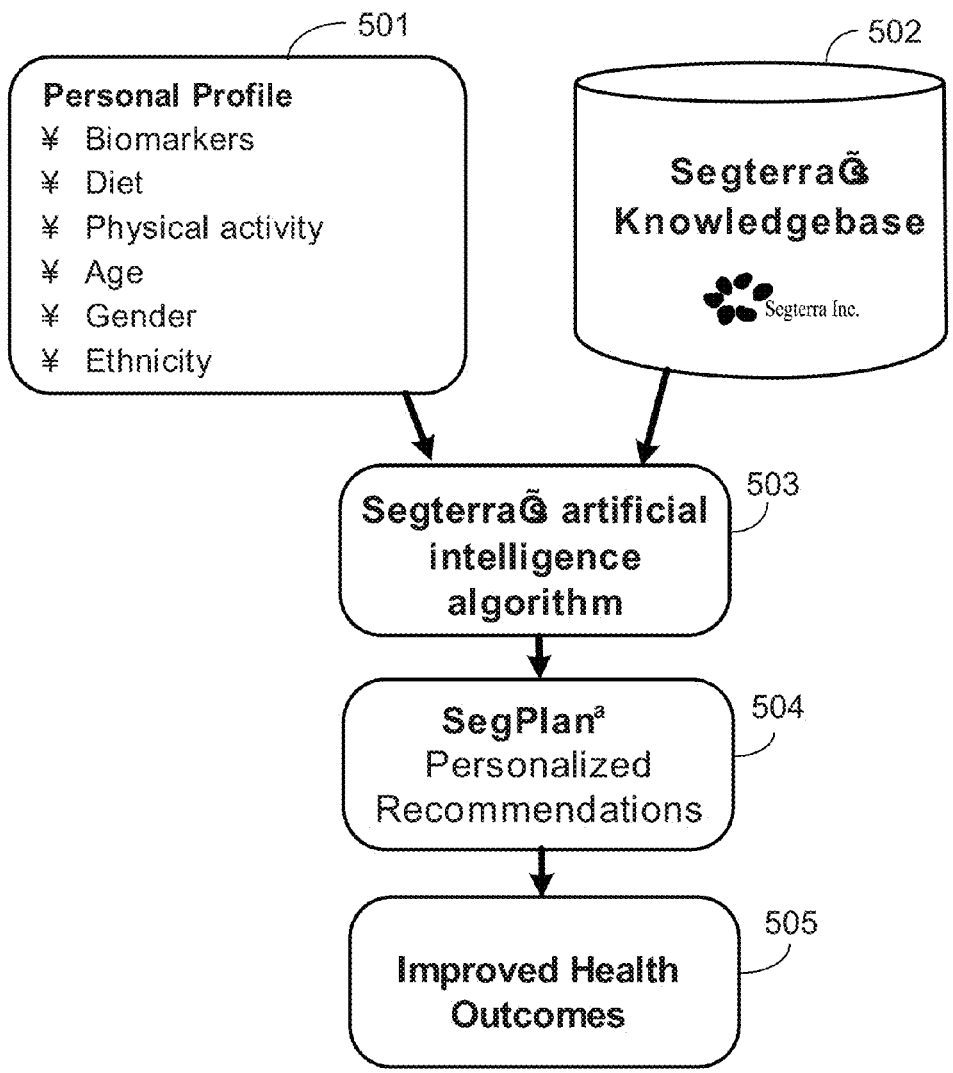
FIG. 5 illustrates an exemplary approach to the invention's personalized recommendations workflow.
Figure 6:
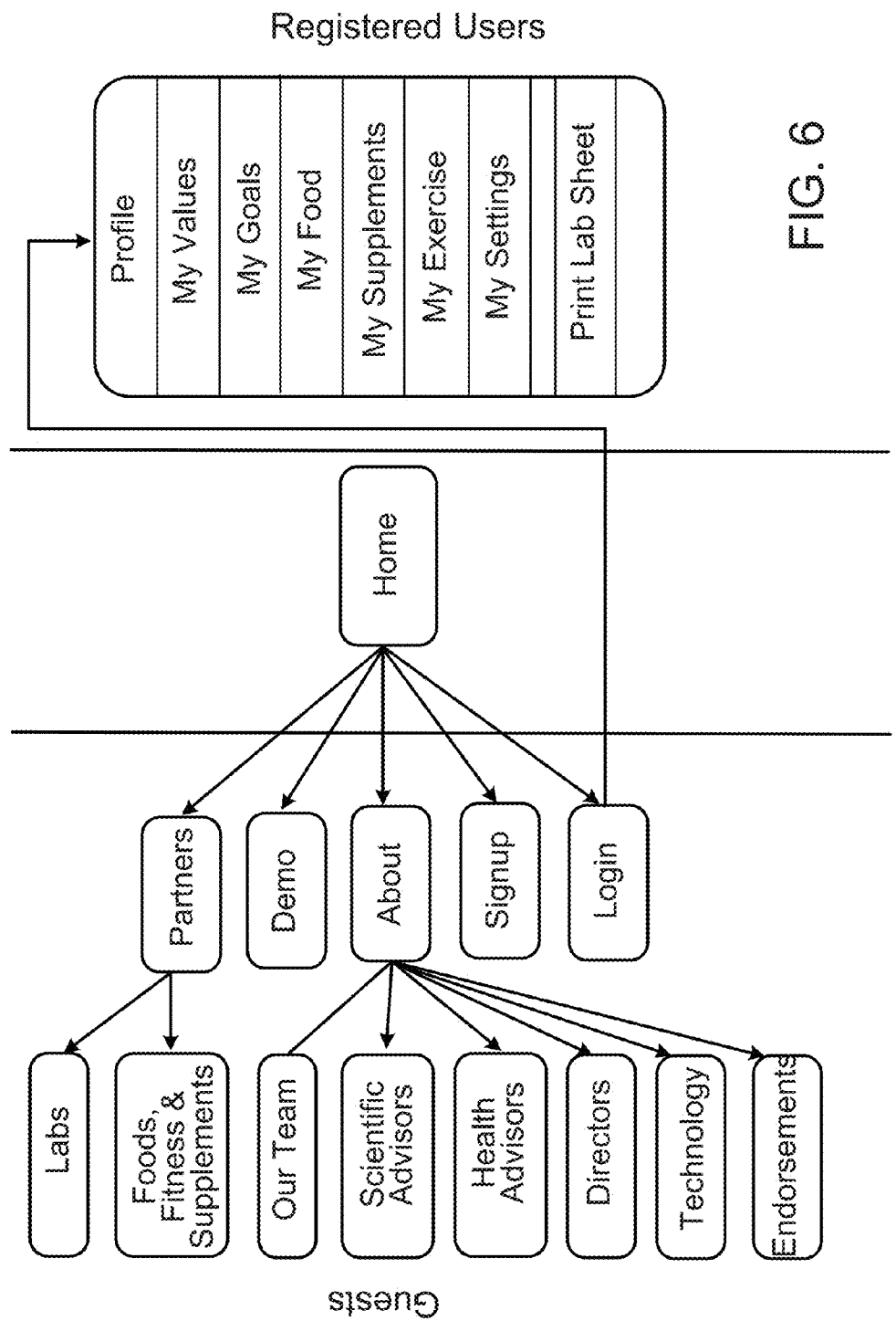
FIG. 6 illustrates an exemplary website workflow in accordance with one embodiment of the invention.

FIG. 5 and FIG. 6 illustrate a representative user experience when utilizing one embodiment of the present invention. In such an embodiment, the user may be able to access a website hosted on a web server providing a graphical user interface allowing the user to dynamically interact with the system or at least an interface to the system. It is foreseen that the user may receive a user name and password to uniquely identify the user and securely connect the user to the system. The user connection may be further secured via a secure socket connection to the web server or through some other common network security protocol. The user may connect to this system via any number of computing devices, including a desktop computer, laptop computer, or smartphone.

In the embodiment of the invention illustrated in FIG. 5, the user may provide her activity level, set goals, initiate blood tests, and view recommendations. The input data derived from the goals and questionnaires may be stored as personal profile 501. Using personal profile 501 together with knowledgebase 502, expert system uses artificial intelligence algorithm 503 to create personalized recommendations 504 which may lead to improved health outcomes 505.

As illustrated in FIG. 6, some website content may be available to all users including guests, while particular content such as a personal profile and personal recommendations may only be available to registered users. It may be desirable to encrypt transmissions between the website and the user when the user is accessing a webpage only accessible to registered users, whereas communication with other webpages may use an unencrypted transmission. It is desirable that site activity be highly interactive. This may include allowing users to drill down into any kind of information: each biomarker, biomarker values, biomarker and biomarker value explanations, and reference to papers or other sources corroborating personal recommendations. The system may be subject to a comprehensive privacy and security policy, comprised of a processes, operating procedures, and technical security safeguards to ensure that the data is safe and only accessible by the intended users.

Corresponding to various parts of the detailed description to this point, a preferred embodiment of the present invention contains the following process workflow:
1. Measure the level of 2 to 100 biomarkers from the user.
2. Use the expert system to generate further qualifying questions about age, ethnicity, exercise, diet etc.
3. User completes the questionnaire.
4. Use the expert system to generate recommendations.
5. Deliver recommendations online.
6. Repeat and refine.

FIG. 7 illustrates an example of biomarker analysis based on a previously published athletic clinical trial and the results of the trial. A putative supplement recommendation is shown below the table as a representation of a fact that may populate a knowledgebase in accordance various embodiments of the present invention. Such a fact may then be used to generate a personalized recommendation as shown boxed in red in FIG. 7. This exemplary analysis illustrates the use of a biochemical blood marker level as input into an inference engine and the construction of personalized dietary intake, supplement, and exercise recommendations as foreseen in various embodiments of the present invention.

Figure 8:
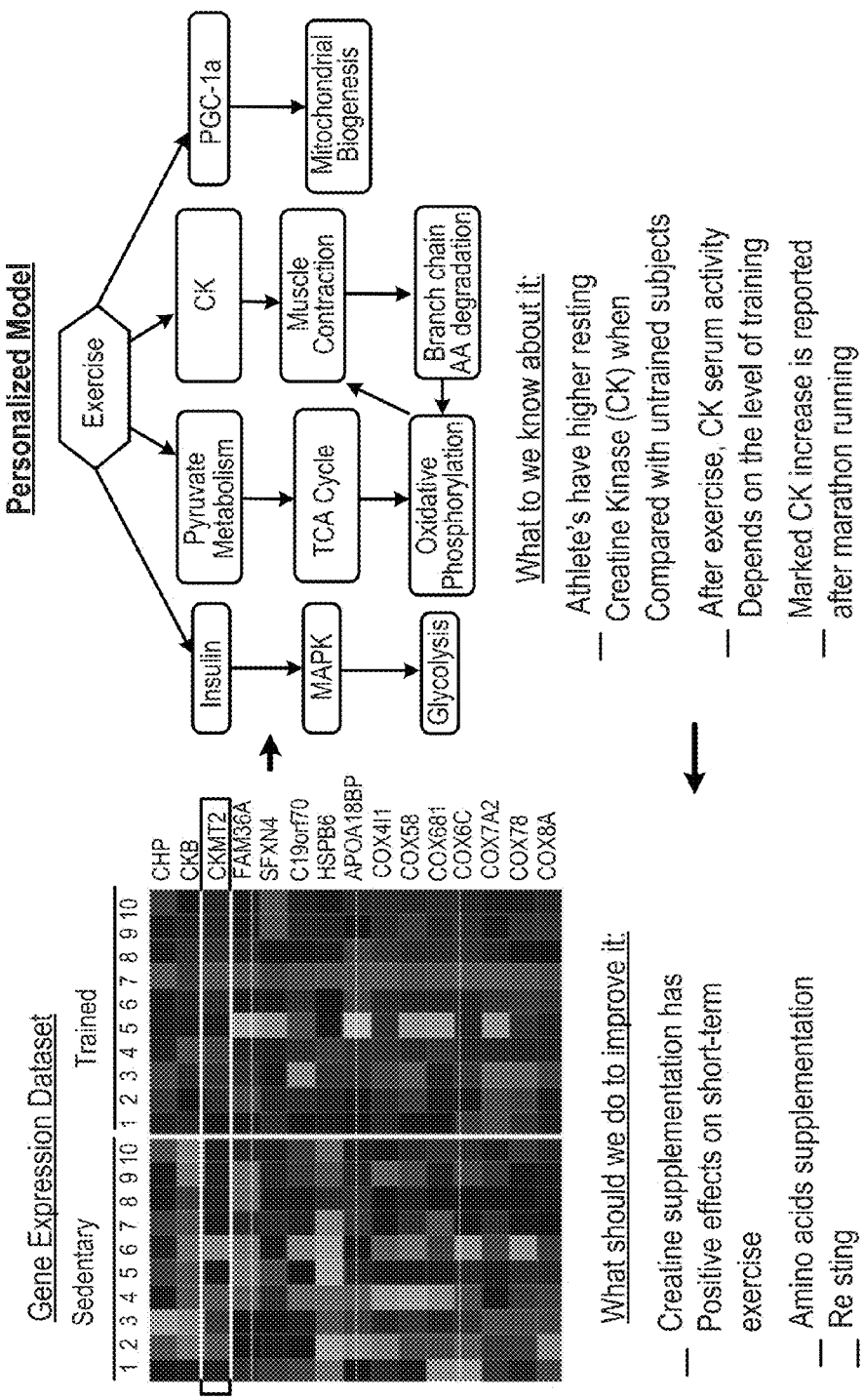
FIG. 8 illustrates an exemplary approach to microarray dataset analysis in accordance with one embodiment of the invention.

As illustrated in FIG. 8, one exemplary embodiment of the present invention ten muscle tissues from sedentary and trained subjects are taken in order to be analyzed using gene expression microarrays. Sedentary subjects are typically defined as subjects who exercise less than 30 min/day twice a week. Trained subjects are typically defined as subjects performing ≥one hour of cycling or running six days a week over the past four years. The upper left panel of the heat map shown in FIG. 8 shows an example of genes that are significantly different between the sedentary and the trained groups. Most of the genes in this example are up-regulated (red) in the trained group and down regulated (green) in the sedentary group. Interestingly, two subjects from the trained group (subjects 3 and 5) have an expression pattern that looks more like the sedentary than the trained. In addition, the expression pattern of subject number 7 of the trained group may indicate over-exercise based on the strong expression changes. Therefore, this panel shows that: 1) exercise induces gene expression change and 2) this response is specific to an individual.

The upper right panel shows the model constructed based on the gene expression results. One of the key processes identified to be up-regulated by exercise by this system biology analysis is creatine kinase (CK). The CK gene, CKMT2, is shown to be up-regulated in most of the trained subjects. The lower right panel shows the current knowledge about CK as a muscle injury marker. The lower left panel presents possible interventions to relieve muscle injury identified by a high level of CK. In summary, this example emphasizes the capabilities of gene expression analysis with a system biology approach to identify relevant athletic markers and to connect those to dietary and exercise interventions in such a way that can be used by various embodiments of the present invention.

In another exemplary embodiment of the present invention, National Health and Nutrition Examination Survey (NHANES) data may be used as input. NHANES data are unique in that they combine blood biomarker levels with information from interviews about life style habits and physical exams. Relevant information about blood biomarkers is extracted from these data and organized by age, gender and ethnicity. FIG. 3 illustrates one entry from the NHANES. The entry as illustrated in FIG. 3 is that of a 20- to 30-year-old Asian male with a prescribed exercise regime and both typical and actual blood levels of ferritin, and Vitamin B12. Such age-, gender- and ethnicity-based criteria may provide additional refinements to the recommendations in various embodiments of the present invention.

The system may also be provided as an article of manufacture having a computer-readable medium with computer-readable instructions embodied thereon for performing the methods and services described in the preceding paragraphs. In some embodiments, the functions may be executed on one or more computers, tablets, smart phones or other computing devices having the processor(s) and memory necessary to implement the system and methods described herein. In some instances, the functionality of methods of the present invention may be embedded on a computer-readable medium, such as, but not limited to, a floppy disk, a hard disk, an optical disk, a magnetic tape, a PROM, an EPROM, CD-ROM, or DVD-ROM or downloaded from a server. The functionality of the techniques may be embedded on the computer-readable medium in any number of computer-readable instructions, or languages such as, for example, FORTRAN, PASCAL, C, C++, PHP, Ruby on Rails, Java, JavaScript, Flash Script, C#, Tcl, BASIC and assembly language and executed by one or more processors. Further, the computer-readable instructions may, for example, be written in a script, macro, or functionally embedded in commercially available software (such as, e.g., EXCEL or VISUAL BASIC).

FIG. 9, FIG. 10, FIG. 11, and FIG. 12 illustrate screen shots of an exemplary website for providing functionality described herein for various embodiments of the present invention.

Appendix A illustrates exemplary biomarkers that could be used in the performance of current invention.

APPENDIX A

| Examples of biomarkers |
|---|
| Marker |
| Adiponectin |
| Adrenocorticotropic Hormone |
| Agouti-Related Protein |
| α-1-Antichymotrypsin |
| α-1-Antitrypsin |
| α-1-Microglobulin |
| α-2-Macroglobulin |
| α-Fetoprotein |
| Amphiregulin |
| Angiopoietin-2 |
| Angiotensin-Converting Enzyme |
| Angiotensinogen |
| Apolipoprotein A-I |
| Apolipoprotein A-II |
| Apolipoprotein A-IV |
| Apolipoprotein B |
| Apolipoprotein C-I |
| Apolipoprotein C-III |
| Apolipoprotein D |
| Apolipoprotein E |
| Apolipoprotein H |
| Apolipoprotein(a) |
| AXL Receptor Tyrosine Kinase |
| B Lymphocyte Chemoattractant |
| β-2-Microglobulin |
| β-cellulin |
| Bone Morphogenetic Protein 6 |
| Brain Natriuretic Peptide |
| Brain-Derived Neurotrophic Factor |
| Calbindin |
| Calcitonin |
| CD 40 antigen |
| CD40 Ligand |
| CD5 |
| Chemokine CC-4 |
| Chromogranin-A |
| Ciliary Neurotrophic Factor |
| Clusterin |
| Complement C3 |
| Complement Factor H |
| Connective Tissue Growth Factor |
| Cortisol |
| C-Peptide |
| C-Reactive Protein |
| Creatine Kinase-MB |
| Cystatin-C |
| Endothelin-1 |
| EN-RAGE |
| Eotaxin-1 |
| Eotaxin-3 |
| Epidermal Growth Factor |
| Epidermal Growth |

APPENDIX A-continued

| Examples of biomarkers |
|---|
| Marker |
| Factor Receptor |
| Epiregulin |
| Epithelial-Derived Neutrophil-Activating Protein 78 |
| Erythropoietin |
| E-Selectin |
| Factor VII |
| Fas Ligand |
| FASLG Receptor |
| Fatty Acid-Binding Protein, heart |
| Ferritin |
| Fetuin-A |
| Fibrinogen |
| Fibroblast Growth Factor 4 |
| Fibroblast Growth Factor basic |
| Follicle-Stimulating Hormone |
| Glucagon |
| Glucagon-like Peptide 1, total |
| Glutathione S-Transferase α |
| Granulocyte Colony-Stimulating Factor |
| Granulocyte-Macrophage Colony-Stimulating Factor |
| Growth Hormone |
| Growth-Regulated α protein |
| Haptoglobin |
| Heat Shock Protein 60 |
| Heparin-Binding EGF-Like Growth Factor |
| Hepatocyte Growth Factor |
| Immunoglobulin A |
| Immunoglobulin E |
| Immunoglobulin M |
| Insulin |
| Insulin-like Growth Factor I |
| Insulin-like Growth Factor-Binding Protein 2 |
| Intercellular Adhesion Molecule 1 |
| Interferon □ |
| Interferon □ Induced Protein 10 |
| IL-1 α |
| IL-1 β |
| IL-1 receptor antagonist |
| IL-10 |
| IL-11 |
| IL-12 Subunit p40 |
| IL-12 Subunit p70 |
| IL-13 |
| IL-15 |
| IL-16 |
| IL-2 |
| IL-25 |
| IL-3 |
| IL-4 |
| IL-5 |
| IL-6 |
| IL-6 receptor |
| IL-7 |

APPENDIX A-continued

Examples of biomarkers

Marker

IL-8
Kidney Injury Molecule-1
Lectin-Like Oxidized LDL Receptor 1
Leptin
Luteinizing Hormone
Lymphotactin
Macrophage Colony-Stimulating Factor 1
Macrophage Inflammatory Protein-1 α
Macrophage Inflammatory Protein-1 α
Macrophage Inflammatory Protein-3 α
Macrophage Migration Inhibitory Factor
Macrophage-Derived Chemokine
Malondialdehyde-Modified Low-Density Lipoprotein
Matrix Metalloproteinase-1
Matrix Metalloproteinase-10
Matrix Metalloproteinase-2
Matrix Metalloproteinase-3
Matrix Metalloproteinase-7
Matrix Metalloproteinase-9
Matrix Metalloproteinase-9, total
Monocyte Chemotactic Protein 1
Monocyte Chemotactic Protein 2
Monocyte Chemotactic Protein 3
Monocyte Chemotactic Protein 4
Monokine Induced by Γ Interferon
Myeloid Progenitor Inhibitory Factor 1
Myeloperoxidase
Myoglobin
Nerve Growth Factor β
Neuronal Cell Adhesion Molecule
Neutrophil Gelatinase-Associated Lipocalin
Osteopontin
Pancreatic Polypeptide
Peptide YY APPENDIX A-continued Examples of biomarkers Marker Placenta Growth Factor
Plasminogen Activator Inhibitor 1
Platelet-Derived Growth Factor BB
Pregnancy-Associated Plasma Protein A
Progesterone
Proinsulin
Prolactin
Prostate-Specific Antigen, Free
Prostatic Acid Phosphatase
Pulmonary and Activation-Regulated Chemokine
RANTES
Receptor for advanced glycosylation end products
Resistin
S100 calcium-binding protein B
Secretin
Serotransferrin
Serum Amyloid P-Component
Serum Glutamic Oxaloacetic Transaminase
Sex Hormone-Binding Globulin
Sortilin
Stem Cell Factor
Superoxide Dismutase 1, soluble
T Lymphocyte-Secreted Protein I-309
Tamm-Horsfall Urinary Glycoprotein
Tenascin-C
Testosterone, Total
Thrombomodulin
Thrombopoietin
Thrombospondin-1
Thymus-Expressed Chemokine
Thyroid-Stimulating Hormone
Thyroxine-Binding Globulin
Tissue Factor
Tissue Inhibitor of Metalloproteinases 1
TNF-Related Apoptosis-Inducing Ligand Receptor 3
Transforming Growth Factor α
Transforming Growth Factor β-3
Transthyretin
Trefoil Factor 3
Tumor Necrosis Factor α
Tumor Necrosis Factor β
Tumor Necrosis Factor Receptor-Like 2
Vascular Cell Adhesion Molecule-1
Vascular Endothelial Growth Factor
Vitamin K-Dependent Protein S
Vitronectin

The invention claimed is:

1. A system for deriving a personalized health and fitness plan for an individual, the system comprising:
    a data storage device for storing (i) an electronic knowledgebase of medical and health data collected from a plurality of sources and (ii) a plurality of questions;
    an inference engine comprising a processor, the inference engine configured to:
        (i) access data for levels of a plurality of biomarkers for the individual,
        (ii) compare the data for the levels of the plurality of biomarkers to the knowledgebase,
        (iii) select a subset of the plurality of questions to be presented to the individual based on one or more of the plurality of biomarkers identified by the comparison,
        (iv) present the selected subset of the plurality of questions to the individual, and
        (v) generate, based on (a) the data for the levels of the plurality of biomarkers and (b) answers received from the individual to the subset of the plurality of questions, a set of recommendations for changing the levels of the one or more of the plurality of biomarkers of the individual; and
    a communication server for transmitting the set of recommendations to the individual over a secure network connection.

2. The system of claim 1, wherein the electronic knowledgebase includes previously collected data for the plurality of biomarkers of the individual.

3. The system of claim 2, wherein the comparison between the knowledgebase and the data for the plurality of biomarkers includes comparison between the data for the plurality of biomarkers and the previously collected data.

4. The system of claim 1, wherein the data for the plurality of biomarkers is collected using a sample of blood from the individual.

5. The system of claim 1, wherein the data for the plurality of biomarkers is collected using a non-blood biological specimen from the individual.

6. The system of claim 1, wherein the plurality of biomarkers comprises creatine kinase.

7. The system of claim 1, wherein the plurality of biomarkers comprises ferritin.

8. The system of claim 1, wherein the subset of the plurality of questions comprises questions about the individual's demographic data.

9. The system of claim 1, wherein the subset of the plurality of questions comprises questions about the individual's athletic activity.

10. The system of claim 1, wherein the set of recommendations comprises dietary recommendations.

11. The system of claim 1, wherein the set of recommendations comprises exercise recommendations.

12. The system of claim 1, wherein the plurality of biomarkers comprises: Creatine Kinase, Magnesium, Calcium, Ferritin, Folate, Vitamin B 12, Vitamin D, Hemoglobin, Lactic acid, White Blood Cells, IL6, Thiamin, Sodium, Zinc, Glycerol, Glutamine, IL-Ib, sTNFR I, CRP, b-2 micro globulin, Neopterin, and TNF-a.

13. The system of claim 1, wherein the plurality of biomarkers comprises: Beta-2-microglobulin, IL6, Calcium, Calcitonin, Ferritin, Sodium, GCSF, CRP, Folate, IL2, Creatine Kinase, Vitamin B12, ILIb, Magnesium, and Vitamin D.

14. A computer-implemented method for deriving a personalized health and fitness plan for an individual, said method comprising the steps of:
    collecting data for levels of a plurality of biomarkers for the individual;
    comparing the data for the levels of the plurality of biomarkers to an electronic knowledgebase of medical and health data collected from a plurality of sources;
    selecting, using a processor, a series of questions to be presented to the individual based on one or more of the plurality of biomarkers identified by the comparison;
    presenting the series of selected questions to the individual;
    receiving answers to the series of selected questions from the individual;
    generating, based on (a) the data for the plurality of biomarkers and Q) the answers, a set of recommendations for changing the levels of the one or more of the plurality of biomarkers of the individual; and
    transmitting said series of lifestyle recommendations to the individual over a secure network connection.

15. The method of claim 14, further comprising the steps of:
    collecting a second set of data for levels of the plurality of biomarkers for the individual at a time subsequent to the step of transmitting; and
    comparing the data for the plurality of biomarkers to the second set of data in order to determine a difference between the data for the plurality of biomarkers and the second set of data.

16. The method of claim 14, wherein the data for the plurality of biomarkers is collected using a sample of blood from the individual.

17. The method of claim 14, wherein the data for the plurality of biomarkers is collected using a non-blood biological specimen from the individual.

18. The method of claim 14, wherein the plurality of biomarkers comprises creatine kinase.

19. The method of claim 14, wherein the plurality of biomarkers comprises ferritin.

20. The method of claim 14, wherein the plurality of biomarkers comprise: Creatine Kinase, Magnesium, Calcium, Ferritin, Folate, Vitamin B 12, Vitamin D, Hemoglobin, Lactic acid, White Blood Cells, IL6, Thiamin, Sodium, Zinc, Glycerol, Glutamine, IL-1b, sTNFR I, CRP, b-2 micro globulin, Neopterin, and TNF-a.

21. The method of claim 14, wherein the plurality of biomarkers comprise: Beta-2-microglobulin, IL6, Calcium, Calcitonin, Ferritin, Sodium, GCSF, CRP, Folate, IL2, Creatine Kinase, Vitamin B12, IL 1b, Magnesium, and Vitamin D.

22. The method of claim 14, wherein the series of questions comprises questions about the individual's demographic data.

23. The method of claim 14, wherein the series of questions comprises questions about the individual's athletic activity.

24. The method of claim 14, wherein the set of recommendations comprises dietary recommendations.

25. The method of claim 14, wherein the set of recommendations comprises exercise recommendations.

* * * * *

UNITED STATES PATENT AND TRADEMARK OFFICE
CERTIFICATE OF CORRECTION

PATENT NO. : 8,762,167 B2  
APPLICATION NO. : 13/190996  
DATED : June 24, 2014  
INVENTOR(S) : Gil Blander et al.

It is certified that error appears in the above-identified patent and that said Letters Patent is hereby corrected as shown below:

In the Claims

Column 13, Line 59, In Claim 12, delete "IL-Ib" and insert -- IL-1b --

Column 14, Line 2, In Claim 13, delete "BI2," and insert -- B12, --

Column 14, Line 2, In Claim 13, delete "ILIb," and insert -- IL-1b, --

Column 14, Line 19 (Approx.), In Claim 14, delete "Q)" and insert -- (b) --

Signed and Sealed this  
Ninth Day of September, 2014

Michelle K. Lee  
*Deputy Director of the United States Patent and Trademark Office*